United States Patent [19]
Merianos et al.

[11] Patent Number: 5,942,240
[45] Date of Patent: Aug. 24, 1999

[54] ANTIMICROBIAL PRESERVATIVE COMPOSITION

[75] Inventors: John J. Merianos, Middletown; Todd Elder, Rockaway, both of N.J.

[73] Assignee: ISP Chemicals Inc., Chatham, N.J.

[21] Appl. No.: 09/014,780

[22] Filed: Jan. 28, 1998

[51] Int. Cl.[6] ............................. A01N 25/02; A01N 25/12
[52] U.S. Cl. ......................... 424/405; 424/401; 424/409; 424/489; 424/76.8; 514/390; 514/526
[58] Field of Search ..................................... 510/384, 577; 424/405, 409, 401, 489, 404, 76.8; 514/519, 526, 390

[56] References Cited

U.S. PATENT DOCUMENTS 4,964,892  10/1990  Hsu.

*Primary Examiner*—Neil S. Levy
*Attorney, Agent, or Firm*—William J. Davis; Marilyn J. Maue; Walter Katz

[57] ABSTRACT

The antimicrobial preservative composition consisting essentially of (a) from 0.5 to 20 wt. % dihalogenated butane having terminal cyano groups and (b) from 80 to 99.5 wt. % of a heterocyclic poly(hydroxy lower alkylamide) in a weight ratio of between 0.5:2 and 0.5:25 which mixture exhibits a synergistic antimicrobial affect over each of components (a) or (b) taken individually.

14 Claims, No Drawings

ANTIMICROBIAL PRESERVATIVE COMPOSITION

BACKGROUND OF THE INVENTION

This invention relates to a water soluble antimicrobial agent suitable for incorporation into a commercial formulation for control of an extended spectrum of fungi, algae and bacterial microorganisms.

Diazolidinyl urea and dibromo dicyano butane have been used individually as antimicrobial agents in a wide range of applications, including cosmetic and pharmaceutical formulations, household and industrial cleaners, bactericides, fungicides and algaecides in paints, pools, paper pulp, animal dips and washes, latex emulsions and the like. The allowable concentration of dibromo dicyano butane in cosmetic and topical pharmaceutical applications is somewhat limited due to its skin irritating properties, water insolubility and color; the latter being particularly objectionable in cosmetics such as face creams and makeup. On the other hand, diazolidinyl urea is a bactericide less effective against fungi.

Thus, it is the aim of research to develop a colorless, odorless agent for control of a broader spectrum of biological activity which is not harmful to humans and which is effective at low dosage levels so as to minimize dilution and efficacy of other active components present in a formulation.

Accordingly, it is an object of this invention to accomplish all of the above objectives by providing a fast acting antimicrobial composition which is effective in small dosages.

Another object is to provide a long lasting bactericide effective against infectious microorganisms.

Still another object is to provide a non-irritating fungicidal composition which can be obtained by an economical and commercially feasible method of manufacture.

These and other objects and advantages will become apparent form the following description and disclosure.

SUMMARY OF THE INVENTION

In accordance with this invention there is provided a antimicrobial mixture of (a) from 0.5 to 20 wt. % of a dihalogenated butane having two terminal cyano groups and (b) from 80 to 99.5 wt. % of a heterocyclic poly (hydroxylated lower alkyl amide) in a weight ratio of between 0.5:2 and 0.5:25, preferably between about 0.5:3 and about 0.5:10. The halogenated component of the invention can be brominated, chlorinated or iodinated and is preferably a dibrominated, dichlorinated or bromochlorinated compound. The most preferred species is dibromo-1,4-dicyano butane.

DETAILED DESCRIPTION OF THE INVENTION

The heterocyclic component (b) of the present mixture is defined by the formula:

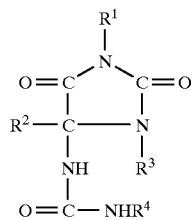

wherein each of $R^1$, $R^2$, $R^3$ and $R^4$ is independently lower alkyl, lower alkyl hydroxy or hydrogen with the proviso that at least one of $R^1$, $R^2$, $R^3$ and $R^4$ is lower alkyl hydroxy. The methyl group is preferred over other lower alkyl groups and diazolidinyl urea is the most preferred heterocyclic species of the invention.

Halogenated component (a) is defined by the formula:

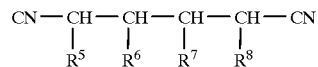

wherein two of $R^5$, $R^6$, $R^7$ and $R^8$ are halo substituents selected from the group of chlorine, bromine and iodine and the remainder of $R^5$, $R^6$, $R^7$ and $R^8$ are hydrogen, with 1,2-dibromo-1,4-dicyano butane being most preferred.

Within the above critical concentrations of components (a) and (b), a mixture of between 0.6 and about 12 wt. % dihalogenated dicyano butane and between about 99.4 and about 88 wt. % of the heterocyclic poly(hydroxyalkyl amide) is preferred. Below 0.5 wt. % of (a), fungicidal control is minimal and is substantially similar to the use of the heterocyclic component alone; whereas above 20 wt. % of (a) its water insolubility asserts its influence on the mixture and uniform distribution of the components in aqueous solutions and formulations is not achieved. Additionally, skin irritation occurs at concentrations above 20 wt. % (a). The ratio of (a) to (b) is also critical for obtaining synergism of the mixture.

The broad spectrum of pathogens controlled by the present antimicrobial mixture encompasses fungi, algae and microorganisms, including gram negative and gram positive bacteria, representative species of which are C. albicans (CAN. ATCC #10231); A. niger (AN, ATCC #16404); P. aeruginosa (PSA. ATCC #9027); E.coli (EC, ATCC #8739); S. aureus (SA. ATCC #6538); B. cepacia (BC, ATCC #25416); red algae, Rhodophyta; Clostridium botulinum, etc.

The concentration of the above mixture in a formulation can vary, depending in part on the degree of infection or infestation and the type of microbe to be controlled. Generally, the antimicrobial mixture can be incorporated in a commercial formulation at a concentration of between about 0.01 and about 3 wt. %, based on total composition. More specifically, for cosmetic or pharmaceutical formulations, the amount of the present mixture need not exceed 1.0 wt. %; however, for industrial or household cleaners, up to 5 wt. % can be employed when desired, depending on the pathogenic nature of the microorganism and the extent of infection.

The present mixture can be conveniently and economically prepared by merely mixing components (a) and (b) under ambient conditions of temperature and pressure until a homogeneous composition is obtained and then freeze dried to provide a free flowing powder. Alternatively, either or both of the components can be dissolved in a mutual solvent before or during mixing to provide a liquid solution or a stable emulsion, suspension or dispersion containing up to about 40% solids. Suitable solvents for the components include alkanols having from 1 to 6 carbon atoms, propylene glycol, butylene glycol, PEG 200–400, phenoxy ethanol and deionized water. Components (a) and/or (b) can be added to the solvent in the desired concentration or the components may be added directly, in a liquid or solid state, to a formulation which contains a suitable solvent or emulsifying agent or emulsifying mixture.

As stated above, the present mixture can be incorporated into a commercial formulation as a dry powder, aqueous dispersion, emulsion or suspension depending on the option of the consumer. When employed as a liquid in aqueous medium, the composition usually contains other excipients such as a wetting agent, emulsifier, anionic or cationic surfactant, etc. and additionally may contain a thickener when desired.

Some typical formulations for the present mixture when employed as an emulsion are the following.

STANDARD EMULSION

| Phase | Ingredient | Wt. % |
|---|---|---|
| A | Stearic Acid | 5.0 |
| A | Mineral Oil | 2.5 |
| A | Cetyl Alcohol | 1.0 |
| A | Laneth-5 + Ceteth-5 + oleth-5 + Steareth-5* | 0.5 |
| A | Glycerol Monostearate + Polyoxyethylene Stearate | 1.5 |
| B | Triethanol amine (99%) | 1.0 |
| D | Citric Acid (30%) | 0.6 |
| C | Present Antimicrobial mixture | 0.1–3 |
| B | Distilled Water | qs |
| | Total | 100.0 |

The above emulsion is prepared by mixing the ingredients of Phase A and heating the mixture to 75° C. Separately mixing and heating the ingredients of Phase B to 75° C. and then adding Phase A to Phase B under constant agitation. Cooling the resulting mixture to about 50° C. before adding C during agitation and then cooling to 40° C. and adding D with continued stirring; after which the mixture is allowed to cool to room temperature. The pH of the emulsion should be about 7.

ANIONIC EMULSION

| Phase | Ingredient | Wt. % |
|---|---|---|
| A | Distilled water | 59.1 |
| A | Carbomer (Crosslinked polymer of acrylic acid) | 10.0 |
| B | Octyl palmitate | 5.0 |
| B | Stearic acid | 3.0 |
| B | Caprylic, caproic triglyceride | 5.0 |
| B | Ethyl, hexyl p-methoxy cinnamate | 5.0 |
| B | Cetearyl alcohol ceteareth-20 | 1.5 |
| B | Cetearyl alcohol | 0.5 |
| C | Triethanolamine (99%) | 1.3 |
| D | Propylene glycol | 4.0 |
| D | Present antimicrobial mixture | 1.6 |
| E | Hydrolyzed Collagen | 0.5 |
| E | Aloe powder 200X | 0.1 |
| E | Distilled water | qs |
| | Total | 100.0% |

The above emulsion was prepared by separately mixing and heating phases A and B to 75° C. and adding phase B to A with continued stirring to obtain a uniform mixture. Phase C is then added followed by Phase D during cooling of the mixture. Finally Phase E is added at 35–40° C. and mixing continued while cooling to room temperature.

NONIONIC EMULSION

| Phase | Ingredient | Wt. % |
|---|---|---|
| A | Distilled water | 69.8 |
| A | Carbomer | 10.0 |
| B | Octyl palmitate | 5.0 |
| B | Cetearyl alcohol Ceteareth-20 | 2.0 |
| B | Glyceryl stearate, Laureth-23 | 2.5 |
| B | Mineral oil | 5.0 |
| C | Triethanolamine (99%) | 0.2 |
| D | Antimicrobial mixture of this invention | 0.5 |
| E | Hydrolyzed Collagen | 0.5 |
| E | Distilled water | qs |
| | Total | 100.0% |

The non-ionic emulsion is prepared by separately mixing and heating Phases A and B to 75° C. and adding Phase B to Phase A with constant stirring to obtain a uniform mixture. Phase C, followed by Phase D are the added and mixed while allowing the mixture to cool. Finally Phase E is added and mixed while the mixture is cooled to room temperature.

A few representative formulations in which the present mixture is employed as the antimicrobial agent include the following.

SHAMPOO

| Ingredient | wt. % |
|---|---|
| Distilled water | qs |
| Blend | 30.00 |
| Sodium laureth sulfate | |
| Sodium lauryl sulfate | |
| Lauramide DEA | |
| Cocamide DEA | |
| Cocamidopropyl betaine | |
| Sodium Cumene sulfonate | |
| Propylene glycol | |
| Citric acid | |
| Blend | 6.00 |
| Sodium laureth sulfate | |
| Glycol distearate | |
| Laureth alcohol | |
| Cocamide MEA | |
| Present antimicrobial mixture | 1.00 |
| Sodium chloride (20% aqueous) | 2.25 |
| Citric acid (20% aqueous) | 0.10 |
| Total | 100.00% |

This formulation is prepared by heating water to 40° C. and adding the remaining ingredients sequentially. The following formulations are similarly prepared.

| Ingredients | wt. % |
|---|---|
| CONTACT LENS CLEANER | |
| Polyhexamethylene biguanide (20% active) HCl salt | 5.0 |
| Microbicidal mixture of this invention | 0.4 |
| Distilled water | qs |
| Total | 100.0% |

-continued

| Ingredients | wt. % |
|---|---|
| DENTURE ADHESIVE | |
| Light mineral oil | 19.0 |
| White petroleum | 19.0 |
| Na/Ca salts of MVE/MA copolymer* | 18.5 |
| Natural non-crosslinked guar | 42.5 |
| Microbicidal mixture of this invention | 1.0 |
| Total | 100.0% |
| HAIR CONDITIONER | |
| 80% aqueous Polyvinylpyrrolidone/silicone oil (80/20) in glycerol stearate + quaternized ammonium surfactant | 3.0 |
| Glycerol stearate wax | 3.5 |
| Cetearyl alcohol | 3.0 |
| Antimicrobicidial mixture of this invention | 0.5 |
| Distilled water | 90.0 |
| Total | 100.0% |
| SYNDET TOILET BAR SOAP | |
| Stearic acid | 36.5 |
| Alkyl amide (Armid HT) | 5.0 |
| Hydrogenated tallow glycerides | 5.0 |
| Sodium cocoyl isethionate | 43.0 |
| Microbicidal mixture of this invention | 3.0 |
| Distilled water | 7.5 |
| Syndet Flakes | 100.0% |
| Perfume | 1.0 |
| Citric acid | 0.6 |
| Water dye solution | 2.5 |
| Titanium dioxide | 0.4 |

*MVE/MA is methyl vinyl ether/maleic anhydride copolymer

The advantageous properties of the present mixture are illustrated by the following test data.

A. WATER SOLUBILITY

The water solubility or insolubility of mixtures of 1,2-dibromo-1,4-dicyano butane (a') to diazolidinyl urea (b') in 1% aqueous solutions at room temperature is shown in following Table I.

TABLE I

| Weight ratio of (a') to (b') | |
|---|---|
| 0.5:99.5 | soluble |
| 0.8:99.2 | soluble |
| 1.0:99.0 | soluble |
| 2.0:98.0 | soluble |
| 5.0:95.0 | soluble |
| 10.0:90.0 | soluble |
| 15.0:85.0 | soluble |
| 20.0:80.0 | soluble |
| 22.0:78.0 | insoluble |

The above results demonstrate that mixtures of (a) to (b) at 20:80 are still soluble; however, with only a 2% increase in the amount of (a), the mixture becomes insoluble.

B. SYNERGISM INDEX OF THE PRESENT MIXTURE

Tables II through VI which follow demonstrate the effective synergistic interaction between components (a) and (b) against a broad range of fungi and gram negative and gram positive bacteria. The Synergism Index was determined by the mathematical treatment of data described by Kull et al. in Applied Microbiology, volume 9, pages 538–541 (1961) using the following formula:

$$\text{Synergism Index (SI)} = QA/Qa + QB/Qb$$

where

QA is the quantity of compound (a) in the mixture, producing an endpoint;

Qa is the quantity of compound (a) acting alone, producing an endpoint;

QB is the quantity of compound (b) in the mixture, producing an endpoint and

Qb is the quantity of compound (b) acting alone, producing an endpoint.

When SI is equal to 1, a mere additive effect of the components in the mixture is indicated; however, when SI is less than 1, synergism has occurred and when SI is greater than 1, antagonism of the two components is indicated. Although the SI is greater than 1 for control of certain organisms, synergistic control of others is still viable as shown by the following data.

According to the above scientifically approved method of determining synergism, the quantity of dibromo-1,4-cyano butane (DBDCB) in the mixture with diazolidonyl urea (DAD) is compared with the quantity of dibromo-1,4-dicyano butane alone which is required to reach the same endpoint, i.e. to produce the same microbiocidal effect as the mixture.

In the following Tables II–VI various concentrations of the present mixture were inoculated with the following pathogens.

TABLE II

| 0.5% DBDCB (0.5:99.5 DBDCB to DAD) | | | | | | |
|---|---|---|---|---|---|---|
| Use Level | Organism | Oa | Ob | OA | OB | SI |
| 0.05 | AN | 1000 | 3200 | 2.5 | 497.5 | 0.16 |
| 0.05 | CAN | 400 | 15000 | 2.5 | 497.5 | 0.04 |
| 0.05 | EC | 500 | 1600 | 2.5 | 497.5 | 0.32 |
| 0.05 | BC | 1500 | 1250 | 2.5 | 497.5 | 0.40 |
| 0.05 | PSA | 500 | 1600 | 2.5 | 497.5 | 0.32 |
| 0.05 | SA | 500 | 1600 | 2.5 | 497.5 | 0.32 |
| 0.1 | AN | 1000 | 3200 | 5 | 995 | 0.32 |
| 0.1 | CAN | 400 | 15000 | 5 | 995 | 0.08 |
| 0.1 | EC | 500 | 1600 | 5 | 995 | 0.63 |
| 0.1 | BC | 1500 | 1250 | S | 995 | 0.80 |
| 0.1 | PSA | 500 | 1600 | 5 | 995 | 0.63 |
| 0.1 | SA | 500 | 1600 | 5 | 995 | 0.63 |
| 0.2 | AN | 1000 | 3200 | 10 | 1990 | 0.63 |
| 0.2 | CAN | 400 | 15000 | 10 | 1990 | 0.16 |
| 0.2 | EC | 500 | 1600 | 10 | 1990 | 1.26 |
| 0.2 | BC | 1500 | 1250 | 10 | 1990 | 1.60 |
| 0.2 | PSA | 500 | 1600 | 10 | 1990 | 1.26 |
| 0.2 | SA | 500 | 1600 | 10 | 1990 | 1.26 |

TABLE III

| 2% DBDCB (2.0:98.0 DBDCB to DAD) | | | | | | |
|---|---|---|---|---|---|---|
| Use Level | Organism | Oa | Ob | OA | OB | SI |
| 0.05 | AN | 1000 | 3200 | 20 | 490 | 0.17 |
| 0.05 | CAN | 400 | 15000 | 20 | 490 | 0.08 |
| 0.05 | EC | 500 | 1600 | 20 | 490 | 0.35 |
| 0.05 | BC | 1500 | 1250 | 20 | 490 | 0.41 |
| 0.05 | PSA | 500 | 1600 | 20 | 490 | 0.35 |
| 0.05 | SA | 500 | 1600 | 20 | 490 | 0.35 |
| 0.1 | AN | 1000 | 3200 | 20 | 980 | 0.33 |
| 0.1 | CAN | 400 | 15000 | 20 | 980 | 0.12 |
| 0.1 | EC | 500 | 1600 | 20 | 980 | 0.65 |
| 0.1 | BC | 1500 | 1250 | 20 | 980 | 0.80 |
| 0.1 | PSA | 500 | 1600 | 20 | 980 | 0.65 |
| 0.1 | SA | 500 | 1600 | 20 | 980 | 0.65 |

TABLE III-continued

2% DBDCB (2.0:98.0 DBDCB to DAD)

| Use Level | Organism | Oa | Ob | OA | OB | SI |
|---|---|---|---|---|---|---|
| 0.2 | AN | 1000 | 3200 | 40 | 1960 | 0.65 |
| 0.2 | CAN | 400 | 15000 | 40 | 1960 | 0.23 |
| 0.2 | EC | 500 | 1600 | 40 | 1960 | 1.31 |
| 0.2 | BC | 1500 | 1250 | 40 | 1960 | 1.59 |
| 0.2 | PSA | 500 | 1600 | 40 | 1960 | 1.31 |
| 0.2 | SA | 500 | 1600 | 40 | 1960 | 1.31 |

TABLE IV

1% DBDCB (1.0:99.0 DBDCB to DAD)

| Use Level | Organism | Oa | Ob | OA | OB | SI |
|---|---|---|---|---|---|---|
| 0.05 | AN | 1000 | 3200 | 5 | 495 | 0.16 |
| 0.05 | CAN | 400 | 15000 | 5 | 495 | 0.05 |
| 0.05 | EC | 500 | 1600 | 5 | 495 | 0.32 |
| 0.05 | BC | 1500 | 1250 | 5 | 495 | 0.40 |
| 0.05 | PSA | 500 | 1600 | 5 | 495 | 0.32 |
| 0.05 | SA | 500 | 1600 | 5 | 495 | 0.32 |
| 0.1 | AN | 1000 | 3200 | 10 | 990 | 0.32 |
| 0.1 | CAN | 400 | 15000 | 10 | 990 | 0.09 |
| 0.1 | EC | 500 | 1600 | 10 | 990 | 0.64 |
| 0.1 | BC | 1500 | 1250 | 10 | 990 | 0.80 |
| 0.1 | PSA | 500 | 1600 | 10 | 990 | 0.64 |
| 0.1 | SA | 500 | 1600 | 10 | 990 | 0.64 |
| 0.2 | AN | 1000 | 3200 | 20 | 1980 | 0.64 |
| 0.2 | CAN | 400 | 15000 | 20 | 1980 | 0.18 |
| 0.2 | EC | 500 | 1600 | 20 | 1980 | 1.28 |
| 0.2 | BC | 1500 | 1250 | 20 | 1980 | 1.60 |
| 0.2 | PSA | 500 | 1600 | 20 | 1980 | 1.28 |
| 0.2 | SA | 500 | 1600 | 20 | 1980 | 1.28 |

TABLE V

10% DBDCB (10.0:90.0 DBDCB to DAD)

| Use Level | Organism | Oa | Ob | OA | OB | SI |
|---|---|---|---|---|---|---|
| 0.05 | AN | 1000 | 3200 | 50 | 450 | 0.19 |
| 0.05 | CAN | 400 | 15000 | 50 | 450 | 0.16 |
| 0.05 | EC | 500 | 1600 | 50 | 450 | 0.38 |
| 0.05 | BC | 1500 | 1250 | 50 | 450 | 0.39 |
| 0.05 | PSA | 500 | 1600 | 50 | 450 | 0.38 |
| 0.05 | SA | 500 | 1600 | 50 | 450 | 0.38 |
| 0.1 | AN | 1000 | 3200 | 100 | 900 | 0.38 |
| 0.1 | CAN | 400 | 15000 | 100 | 900 | 0.31 |
| 0.1 | EC | 500 | 1600 | 100 | 900 | 0.76 |
| 0.1 | BC | 1500 | 1250 | 100 | 900 | 0.79 |
| 0.1 | PSA | 500 | 1600 | 100 | 900 | 0.76 |
| 0.1 | SA | 500 | 1600 | 100 | 900 | 0.76 |
| 0.2 | AN | 1000 | 3200 | 200 | 1800 | 0.76 |
| 0.2 | CAN | 400 | 15000 | 200 | 1800 | 0.62 |
| 0.2 | EC | 500 | 1600 | 200 | 1800 | 1.53 |
| 0.2 | BC | 1500 | 1250 | 200 | 1800 | 1.57 |
| 0.2 | PSA | 500 | 1600 | 200 | 1800 | 1.53 |
| 0.2 | SA | 500 | 1600 | 200 | 1800 | 1.53 |

TABLE VI

5% DBDCB (5.0:95.0 DBDCB to DAD)

| Use Level | Organism | Oa | Ob | OA | OB | SI |
|---|---|---|---|---|---|---|
| 0.05 | AN | 1000 | 3200 | 25 | 475 | 0.17 |
| 0.05 | CAN | 400 | 15000 | 25 | 475 | 0.09 |
| 0.05 | EC | 500 | 1600 | 25 | 475 | 0.35 |
| 0.05 | BC | 1500 | 1250 | 25 | 475 | 0.40 |
| 0.05 | PSA | 500 | 1600 | 25 | 475 | 0.35 |
| 0.05 | SA | 500 | 1600 | 25 | 475 | 0.35 |
| 0.1 | AN | 1000 | 3200 | 50 | 950 | 0.35 |
| 0.1 | CAN | 400 | 15000 | 50 | 950 | 0.19 |
| 0.1 | EC | 500 | 1600 | 50 | 950 | 0.69 |
| 0.1 | BC | 1500 | 1250 | 50 | 950 | 0.79 |
| 0.1 | PSA | 500 | 1600 | 50 | 950 | 0.69 |
| 0.1 | SA | 500 | 1600 | 50 | 950 | 0.69 |
| 0.2 | AN | 1000 | 3200 | 100 | 1900 | 0.69 |
| 0.2 | CAN | 400 | 15000 | 100 | 1900 | 0.38 |
| 0.2 | EC | 500 | 1600 | 100 | 1900 | 1.39 |
| 0.2 | BC | 1500 | 1250 | 100 | 1900 | 1.59 |
| 0.2 | PSA | 500 | 1600 | 100 | 1900 | 1.39 |
| 0.2 | SA | 500 | 1600 | 100 | 1900 | 1.39 |

PRESERVATIVE ACTIVITY (CHALLENGE TEST)

A typical cosmetic emulsion was prepared for microbiological challenge testing and predetermined admixtures of a methylol compound and IPBC were added at various use levels. The emulsion thus prepared had the following composition:

| | % wt. |
|---|---|
| Phase A | |
| Stearic Acid | 5.00 |
| Mineral Oil | 2.50 |
| Cetyl Alcohol | 1.00 |
| Lareth-5 and Ceteth-5 and Steareth-5 | 0.50 |
| Glycerol Monostearate and Polyoxyethylene Stearate | 1.50 |
| Phase B | |
| Deionized Water | 88.0 |
| Triethanolamine 99% | 1.0 |
| Citric Acid 30% aqueous solution | 0.60 |
| Preservative Admixture | qs |

To prepare the emulsion, Phases A and B were heated separately to 75°–80° C. Phase A then was added to Phase B with mixing. The mixture then was cooled to 55°–60° C. At this point the desired amount of the preservative admixture was added and the product was cooled to 50° C. while stirring. The citric acid solution then was added to adjust the pH and the mixture was stirred until a temperature of 30° C. was reached.

The challenge tests were carried out using the following microorganisms: SA, ECOLI, PSA, PC, AN and CAN, in this manner. 50 g aliquots of the test emulsion containing various amounts of the preservative admixture were inoculated with approximately $10^7$–$10^8$ of the challenge organisms. The test samples then were stirred to disperse the challenge inoculum. The samples were incubated and assayed at 48 hours, 7, 14, 21 and 28 days. The assays were performed on 1 g of the test sample by serially diluting $10^1$ to $10^6$ of the original concentration. The plating medium for bacteria was Letheen agar and for fungi it was low pH Mycophil agar with Tween 20. Each plated sample was incubated for 48 hours at 37° C. for bacteria, 5 days at 25° C. for mold, and 3 days at 25° C. for fungi. After incubation, readings of the number of colonies per milliliter (cfu/ml) were made. At 21 days the test product was reinoculated with half of the original inoculum. The data is presented in Tables VII–XVII below.

Tables VII–X are in the Standard Emulsion

TABLE VII

1:99 DBDCB/Diazolidinyl Urea

| Test Level | Organism | 48 Hours | 7 Days | 14 Days | 21 Days | 28 Days |
|---|---|---|---|---|---|---|
| 0.05% | AN | <10 | <10 | <10 | <10 | <10 |
| 0.05% | CAN | 3,100 | 70 | <10 | <10 | 14,000 |
| 0.05% | EC | <10 | <10 | <10 | <10 | <10 |
| 0.05% | BC | <10 | <10 | <10 | <10 | <10 |
| 0.05% | PSA | <10 | <10 | <10 | <10 | <10 |
| 0.05% | SA | 6,300 | <10 | <10 | <10 | <10 |
| 0.10% | AN | <10 | <10 | <10 | <10 | <10 |
| 0.10% | CAN | 100 | <10 | <10 | <10 | <10 |
| 0.10% | EC | <10 | <10 | <10 | <10 | <10 |
| 0.10% | BC | <10 | <10 | <10 | <10 | <10 |
| 0.10% | PSA | <10 | <10 | <10 | <10 | <10 |
| 0.10% | SA | 80 | <10 | <10 | <10 | <10 |
| 0.20% | AN | <10 | <10 | <10 | <10 | <10 |
| 0.20% | CAN | <10 | <10 | <10 | <10 | <10 |
| 0.20% | EC | <10 | <10 | <10 | <10 | <10 |
| 0.20% | BC | <10 | <10 | <10 | <10 | <10 |
| 0.20% | PSA | <10 | <10 | <10 | <10 | <10 |
| 0.20% | SA | <10 | <10 | <10 | <10 | <10 |

Unpreserved Control

| Organism | 48 Hours | 7 Days | 14 Days |
|---|---|---|---|
| AN | 58,000 | 42,000 | 420,000 |
| CAN | 160,000 | 83,000 | 470,000 |
| EC | 1,400,000 | 3,800,000 | 3,800,000 |
| BC | 36,000,000 | 30,000,000 | 18,000,000 |
| PSA | 120 | 45,000 | 45,000 |
| SA | 7,500,000 | 93,000 | 1,600 |

Inoculum Concentration

| Organism | 0 Hours | 21 Days |
|---|---|---|
| AN | 20,000 | 120,000 |
| CAN | 3,400,000 | 250,000,000 |
| EC | 6,100,000 | 9,000,000 |
| BC | 230,000 | 30,000,000 |
| PSA | 3,500,000 | 11,000,000 |
| SA | 4,000,000 | 11,000,000 |

TABLE VIII

1:999 DBDCB/Diazolidinyl Urea

| Test Level | Organism | 48 Hours | 7 Days | 14 Days | 21 Days | 28 Days |
|---|---|---|---|---|---|---|
| 0.05% | AN | <10 | <10 | <10 | <10 | <10 |
| 0.05% | CAN | 6,300 | 60 | 10 | 10 | 22,000 |
| 0.05% | EC | 270 | <10 | <10 | <10 | <10 |
| 0.05% | BC | <10 | <10 | <10 | <10 | <10 |
| 0.05% | PSA | <10 | <10 | <10 | <10 | <10 |
| 0.05% | SA | 5,300 | <10 | <10 | <10 | <10 |
| 0.10% | AN | <10 | <10 | <10 | <10 | <10 |
| 0.10% | CAN | 200 | 10 | <10 | <10 | <10 |
| 0.10% | EC | 20 | <10 | <10 | <10 | <10 |
| 0.10% | BC | <10 | <10 | <10 | <10 | <10 |
| 0.10% | PSA | <10 | <10 | <10 | <10 | <10 |
| 0.10% | SA | 400 | <10 | <10 | <10 | <10 |
| 0.20% | AN | <10 | <10 | <10 | <10 | <10 |
| 0.20% | CAN | <10 | <10 | <10 | <10 | <10 |
| 0.20% | EC | <10 | <10 | <10 | <10 | <10 |
| 0.20% | BC | <10 | <10 | <10 | <10 | <10 |
| 0.20% | PSA | <10 | <10 | <10 | <10 | <10 |
| 0.20% | SA | <10 | <10 | <10 | <10 | <10 |

Unpreserved Control

| Organism | 48 Hours | 7 Days | 14 Days |
|---|---|---|---|
| AN | 58,000 | 42,000 | 420,000 |
| CAN | 160,000 | 83,000 | 470,000 |
| EC | 1,400,000 | 3,800,000 | 3,800,000 |
| BC | 36,000,000 | 30,000,000 | 18,000,000 |
| PSA | 120 | 45,000 | 45,000 |
| SA | 7,500,000 | 93,000 | 1,600 |

Inoculum Concentration

| Organism | 0 Hours | 21 Days |
|---|---|---|
| AN | 20,000 | 120,000 |
| CAN | 3,400,000 | 250,000,000 |
| EC | 6,100,000 | 9,000,000 |
| BC | 230,000 | 30,000,000 |
| PSA | 3,500,000 | 11,000,000 |
| SA | 4,000,000 | 11,000,000 |

TABLE IX

1:4 DBDCB/Diazolidinyl Urea

| Test Level | Organism | 48 Hours | 7 Days | 14 Days | 21 Days | 28 Days |
|---|---|---|---|---|---|---|
| 0.05% | AN | <10 | <10 | <10 | <10 | <10 |
| 0.05% | CAN | 50 | <10 | <10 | <10 | <10 |
| 0.05% | EC | <10 | <10 | <10 | <10 | <10 |
| 0.05% | BC | <10 | <10 | <10 | <10 | <10 |
| 0.05% | PSA | <10 | <10 | <10 | <10 | <10 |
| 0.05% | SA | 50 | <10 | <10 | <10 | <10 |
| 0.10% | AN | <10 | <10 | <10 | <10 | <10 |
| 0.10% | CAN | <10 | <10 | <10 | <10 | <10 |
| 0.10% | EC | <10 | <10 | <10 | <10 | <10 |
| 0.10% | BC | <10 | <10 | <10 | <10 | <10 |
| 0.10% | PSA | <10 | <10 | <10 | <10 | <10 |
| 0.10% | SA | <10 | <10 | <10 | <10 | <10 |
| 0.20% | AN | <10 | <10 | <10 | <10 | <10 |
| 0.20% | CAN | <10 | <10 | <10 | <10 | <10 |
| 0.20% | EC | <10 | <10 | <10 | <10 | <10 |
| 0.20% | BC | <10 | <10 | <10 | <10 | <10 |
| 0.20% | PSA | <10 | <10 | <10 | <10 | <10 |
| 0.20% | SA | <10 | <10 | <10 | <10 | <10 |

Unpreserved Control

| Organism | 48 Hours | 7 Days | 14 Days |
|---|---|---|---|
| AN | 58,000 | 42,000 | 420,000 |
| CAN | 160,000 | 83,000 | 470,000 |
| EC | 1,400,000 | 3,800,000 | 3,800,000 |
| BC | 36,000,000 | 30,000,000 | 18,000,000 |
| PSA | 120 | 45,000 | 45,000 |
| SA | 7,500,000 | 93,000 | 1,600 |

Inoculum Concentration

| Organism | 0 Hours | 21 Days |
|---|---|---|
| AN | 14,000 | 20,000 |
| CAN | 240,000 | 340,000 |
| EC | 640,000 | 6,100,000 |
| BC | 690000 | 120,000 |
| PSA | 1,100,000 | 3,500,000 |
| SA | 1,100,000 | 4,000,000 |

TABLE X

1:9 DBDCB/Diazolidinyl Urea

| Test Level | Organism | 48 Hours | 7 Days | 14 Days | 21 Days | 28 Days |
|---|---|---|---|---|---|---|
| 0.05% | AN | <10 | <10 | <10 | <10 | <10 |
| 0.05% | CAN | <10 | <10 | <10 | <10 | <10 |
| 0.05% | EC | <10 | <10 | <10 | <10 | <10 |
| 0.05% | BC | <10 | <10 | <10 | <10 | <10 |
| 0.05% | PSA | <10 | <10 | <10 | <10 | <10 |
| 0.05% | SA | 10 | <10 | <10 | <10 | <10 |
| 0.10% | AN | <10 | <10 | <10 | <10 | <10 |
| 0.10% | CAN | <10 | <10 | <10 | <10 | <10 |
| 0.10% | EC | <10 | <10 | <10 | <10 | <10 |
| 0.10% | BC | <10 | <10 | <10 | <10 | <10 |
| 0.10% | PSA | <10 | <10 | <10 | <10 | <10 |
| 0.10% | SA | 100 | <10 | <10 | <10 | <10 |
| 0.20% | AN | <10 | <10 | <10 | <10 | <10 |
| 0.20% | CAN | <10 | <10 | <10 | <10 | <10 |
| 0.20% | EC | <10 | <10 | <10 | <10 | <10 |
| 0.20% | BC | <10 | <10 | <10 | <10 | <10 |
| 0.20% | PSA | <10 | <10 | <10 | <10 | <10 |
| 0.20% | SA | <10 | <10 | <10 | <10 | <10 |

Unpreserved Control

| Organism | 48 Hours | 7 Days | 14 Days |
|---|---|---|---|
| AN | 58,000 | 42,000 | 420,000 |
| CAN | 160,000 | 83,000 | 470,000 |
| EC | 1,400,000 | 3,800,000 | 3,800,000 |
| BC | 36,000,000 | 30,000,000 | 18,000,000 |
| PSA | 120 | 45,000 | 45,000 |
| SA | 7,500,000 | 93,000 | 1,600 |

Inoculum Concentration

| Organism | 0 Hours | 21 Days |
|---|---|---|
| AN | 14,000 | 20,000 |
| CAN | 240,000 | 340,000 |
| EC | 640,000 | 6,100,000 |
| BC | 690000 | 120,000 |
| PSA | 1,100,000 | 3,500,000 |
| SA | 1,100,000 | 4,000,000 |

Tables XI–XII are in a Anion Emulsion

TABLE XI

6:94 DBDCB/Diazolidinyl Urea

| Test Level | Organism | 48 Hours | 7 Days | 14 Days | 21 Days | 28 Days |
|---|---|---|---|---|---|---|
| 0.05% | AN | 17000 | 100 | <10 | <10 | <10 |
| 0.05% | CAN | 47,000 | 25,000 | 320,000 | 230,000 | 6,000,000 |
| 0.05% | EC | 350,000 | <10 | <10 | <10 | <10 |
| 0.05% | BC | <10 | <10 | <10 | <10 | <10 |
| 0.05% | PSA | <10 | <10 | <10 | <10 | <10 |
| 0.05% | SA | 6,300 | <10 | <10 | <10 | <10 |
| 0.10% | AN | <10 | <10 | <10 | <10 | <10 |
| 0.10% | CAN | 2,500 | 2,100 | 19,000 | 70,000 | 80,000 |
| 0.10% | EC | <10 | <10 | <10 | <10 | <10 |
| 0.10% | BC | <10 | <10 | <10 | <10 | <10 |
| 0.10% | PSA | <10 | <10 | <10 | <10 | <10 |
| 0.10% | SA | 590 | <10 | <10 | <10 | <10 |
| 0.20% | AN | <10 | <10 | <10 | <10 | <10 |
| 0.20% | CAN | <10 | <10 | <10 | <10 | <10 |
| 0.20% | EC | <10 | <10 | <10 | <10 | <10 |
| 0.20% | BC | <10 | <10 | <10 | <10 | <10 |
| 0.20% | PSA | <10 | <10 | <10 | <10 | <10 |
| 0.20% | SA | <10 | <10 | <10 | <10 | <10 |

Unpreserved Control

| Organism | 48 Hours | 7 Days | 14 Days |
|---|---|---|---|
| AN | 180,000 | 700,000 | 1,500,000 |
| CAN | 2,800,000 | 6,000,000 | 2,100,000 |
| EC | 100,000,000 | 100,000,000 | 100,000,000 |
| BC | 100,000,000 | 100,000,000 | 100,000,000 |
| PSA | 100,000,000 | 100,000,000 | 100,000,000 |
| SA | 100,000,000 | 100,000,000 | 76,000,000 |

Inoculum Concentration

| Organism | 0 Hours | 21 Days |
|---|---|---|
| AN | 80,000 | 150,000 |
| CAN | 630,000 | 1,900,000 |
| EC | 1,900,000 | 2,400,000 |
| BC | 1,900,000 | 4,000,000 |
| PSA | 2,300,000 | 3,600,000 |
| SA | 700,000 | 2,100,000 |

TABLE XII

12:88 DBDCB/Diazolidinyl Urea

| Test Level | Organism | 48 Hours | 7 Days | 14 Days | 21 Days | 28 Days |
|---|---|---|---|---|---|---|
| 0.05% | AN | 17000 | 100 | <10 | <10 | 20 |
| 0.05% | CAN | 51,000 | 1,500 | 1,000 | <10 | 7,200 |
| 0.05% | EC | 4,800 | <10 | <10 | <10 | <10 |
| 0.05% | BC | <10 | <10 | <10 | <10 | <10 |
| 0.05% | PSA | <10 | <10 | <10 | <10 | <10 |
| 0.05% | SA | 50,000 | <10 | <10 | <10 | <10 |
| 0.10% | AN | <10 | <10 | <10 | <10 | <10 |
| 0.10% | CAN | 80 | <10 | <10 | <10 | 20 |
| 0.10% | EC | <10 | <10 | <10 | <10 | <10 |
| 0.10% | BC | <10 | <10 | <10 | <10 | <10 |
| 0.10% | PSA | <10 | <10 | <10 | <10 | <10 |
| 0.10% | SA | 590 | <10 | <10 | <10 | <10 |
| 0.20% | AN | <10 | <10 | <10 | <10 | <10 |
| 0.20% | CAN | <10 | <10 | <10 | <10 | <10 |
| 0.20% | EC | <10 | <10 | <10 | <10 | <10 |
| 0.20% | BC | <10 | <10 | <10 | <10 | <10 |
| 0.20% | PSA | <10 | <10 | <10 | <10 | <10 |
| 0.20% | SA | <10 | <10 | <10 | <10 | <10 |

Unpreserved Control

| Organism | 48 Hours | 7 Days | 14 Days |
|---|---|---|---|
| AN | 180,000 | 700,000 | 1,500,000 |
| CAN | 2,800,000 | 6,000,000 | 2,100,000 |
| EC | 100,000,000 | 100,000,000 | 100,000,000 |
| BC | 100,000,000 | 100,000,000 | 100,000,000 |
| PSA | 100,000,000 | 100,000,000 | 100,000,000 |
| SA | 100,000,000 | 100,000,000 | 76,000,000 |

Inoculum Concentration

| Organism | 0 Hours | 21 Days |
|---|---|---|
| AN | 80,000 | 150,000 |
| CAN | 630,000 | 1,900,000 |
| EC | 1,900,000 | 2,400,000 |
| BC | 1,900,000 | 4,000,000 |
| PSA | 2,300,000 | 3,600,000 |
| SA | 700,000 | 2,100,000 |

Tables XIII–XVI are in a Nonion Emulsion

TABLE XIII

1:49 DBDCB/Diazolidinyl Urea

| Test Level | Organism | 48 Hours | 7 Days | 14 Days | 21 Days | 28 Days |
|---|---|---|---|---|---|---|
| 0.05% | AN | 160 | <10 | <10 | <10 | 30 |
| 0.05% | CAN | 43,000 | 3,400,000 | 3,400,000 | 16000000 | 29,000,000 |
| 0.05% | EC | 4,600 | <10 | <10 | <10 | <10 |
| 0.05% | BC | <10 | <10 | <10 | <10 | <10 |
| 0.05% | PSA | <10 | <10 | <10 | <10 | <10 |
| 0.05% | SA | 1,100 | <10 | <10 | <10 | <10 |
| 0.10% | AN | <10 | <10 | <10 | <10 | <10 |
| 0.10% | CAN | <10 | 320 | 84,000 | 510,000 | 33,000,000 |
| 0.10% | EC | 30 | <10 | <10 | <10 | <10 |
| 0.10% | BC | <10 | <10 | <10 | <10 | <10 |
| 0.10% | PSA | <10 | <10 | <10 | <10 | <10 |
| 0.10% | SA | 590 | <10 | <10 | <10 | <10 |
| 0.20% | AN | <10 | <10 | <10 | <10 | <10 |
| 0.20% | CAN | <10 | <10 | <10 | <10 | <10 |
| 0.20% | EC | <10 | <10 | <10 | <10 | <10 |
| 0.20% | BC | <10 | <10 | <10 | <10 | <10 |
| 0.20% | PSA | <10 | <10 | <10 | <10 | <10 |
| 0.20% | SA | <10 | <10 | <10 | <10 | <10 |

Unpreserved Control

| Organism | 48 Hours | 7 Days | 14 Days |
|---|---|---|---|
| AN | 150,000 | 160,000 | 160,000 |
| CAN | 2,400,000 | 420,000 | 420,000 |
| EC | 100,000,000 | 100,000,000 | 1,000,000 |
| BC | 100,000,000 | 100,000,000 | 1,000,000 |
| PSA | 100,000,000 | 100,000,000 | 1,000,000 |
| SA | 9,700,000 | 520,000 | 630 |

Inoculum Concentration

| Organism | 0 Hours | 21 Days |
|---|---|---|
| AN | 190,000 | 26,000 |
| CAN | 1,900,000 | 380,000 |
| EC | 4,600,000 | 700,000 |
| BC | 5,200,000 | 310,000 |
| PSA | 5,200,000 | 14,000,000 |
| SA | 8,400,000 | 960,000 |

TABLE XIV

1:20 DBDCB/Diazolidinyl Urea

| Test Level | Organism | 48 Hours | 7 Days | 14 Days | 21 Days | 28 Days |
|---|---|---|---|---|---|---|
| 0.05% | AN | 90 | <10 | <10 | <10 | 60 |
| 0.05% | CAN | 180 | 220 | 3,600 | 320,000 | 120,000,000 |
| 0.05% | EC | 1,500 | <10 | <10 | <10 | <10 |
| 0.05% | BC | <10 | <10 | <10 | <10 | <10 |
| 0.05% | PSA | <10 | <10 | <10 | <10 | <10 |
| 0.05% | SA | 1,200 | <10 | <10 | <10 | <10 |
| 0.10% | AN | <10 | <10 | <10 | <10 | <10 |
| 0.10% | CAN | <10 | <10 | <10 | <10 | <10 |
| 0.10% | EC | <10 | <10 | <10 | <10 | <10 |
| 0.10% | BC | <10 | <10 | <10 | <10 | <10 |
| 0.10% | PSA | <10 | <10 | <10 | <10 | <10 |
| 0.10% | SA | <10 | <10 | <10 | <10 | <10 |
| 0.20% | AN | <10 | <10 | <10 | <10 | <10 |
| 0.20% | CAN | <10 | <10 | <10 | <10 | <10 |
| 0.20% | EC | <10 | <10 | <10 | <10 | <10 |
| 0.20% | BC | <10 | <10 | <10 | <10 | <10 |
| 0.20% | PSA | <10 | <10 | <10 | <10 | <10 |
| 0.20% | SA | <10 | <10 | <10 | <10 | <10 |

TABLE XIV-continued

1:20 DBDCB/Diazolidinyl Urea
Unpreserved Control

| Organism | 48 Hours | 7 Days | 14 Days |
|---|---|---|---|
| AN | 150,000 | 160,000 | 160,000 |
| CAN | 2,400,000 | 420,000 | 420,000 |
| EC | 100,000,000 | 100,000,000 | 1,000,000 |
| BC | 100,000,000 | 100,000,000 | 1,000,000 |
| PSA | 100,000,000 | 100,000,000 | 1,000,000 |
| SA | 9,700,000 | 520,000 | 630 |

Inoculum Concentration

| Organism | 0 Hours | 21 Days |
|---|---|---|
| AN | 190,000 | 26,000 |
| CAN | 1,900,000 | 380,000 |
| EC | 4,600,000 | 700,000 |
| BC | 5,200,000 | 310,000 |
| PSA | 5,200,000 | 14,000,000 |
| SA | 8,400,000 | 960,000 |

TABLE XV

6:94 DBDCB/Diazolidinyl Urea

| Test Level | Organism | 48 Hours | 7 Days | 14 Days | 21 Days | 28 Days |
|---|---|---|---|---|---|---|
| 0.05% | AN | 30 | <10 | <10 | <10 | 20 |
| 0.05% | CAN | <10 | 20 | 380 | 36,000 | 90,000 |
| 0.05% | EC | 230 | <10 | <10 | <10 | <10 |
| 0.05% | BC | <10 | <10 | <10 | <10 | <10 |
| 0.05% | PSA | <10 | <10 | <10 | <10 | <10 |
| 0.05% | SA | 71,000 | <10 | <10 | <10 | <10 |
| 0.10% | AN | <10 | <10 | <10 | <10 | <10 |
| 0.10% | CAN | <10 | <10 | <10 | <10 | 130,000 |
| 0.10% | EC | <10 | <10 | <10 | <10 | <10 |
| 0.10% | BC | <10 | <10 | <10 | <10 | <10 |
| 0.10% | PSA | <10 | <10 | <10 | <10 | <10 |
| 0.10% | SA | 60 | <10 | <10 | <10 | <10 |
| 0.20% | AN | <10 | <10 | <10 | <10 | <10 |
| 0.20% | CAN | <10 | <10 | <10 | <10 | <10 |
| 0.20% | EC | <10 | <10 | <10 | <10 | <10 |
| 0.20% | BC | <10 | <10 | <10 | <10 | <10 |
| 0.20% | PSA | <10 | <10 | <10 | <10 | <10 |
| 0.20% | SA | <10 | <10 | <10 | <10 | <10 |

Unpreserved Control

| Organism | 48 Hours | 7 Days | 14 Days |
|---|---|---|---|
| AN | 160,000 | 40,000 | 40,000 |
| CAN | 4,400,000 | 960,000 | 1,000,000 |
| EC | 100,000,000 | 1,000,000 | 1,000,000 |
| BC | 100,000,000 | 1,000,000 | 1,000,000 |
| PSA | 100,000,000 | 1,000,000 | 1,000,000 |
| SA | 27,000,000 | 9,1000 | 6,500 |

Inoculum Concentration

| Organism | 0 Hours | 21 Days |
|---|---|---|
| AN | 190,000 | 26,000 |
| CAN | 1,900,000 | 380,000 |
| EC | 4,600,000 | 700,000 |
| BC | 5,200,000 | 310,000 |
| PSA | 5,200,000 | 14,000,000 |
| SA | 8,400,000 | 960,000 |

TABLE XVI

12:88 DBDCB/Diazolidinyl Urea

| Test Level | Organism | 48 Hours | 7 Days | 14 Days | 21 Days | 28 Days |
|---|---|---|---|---|---|---|
| 0.05% | AN | 70 | <10 | <10 | <10 | 10 |
| 0.05% | CAN | <10 | <10 | <10 | <10 | <10 |
| 0.05% | EC | 150 | <10 | <10 | <10 | <10 |
| 0.05% | BC | <10 | <10 | <10 | <10 | <10 |
| 0.05% | PSA | <10 | <10 | <10 | <10 | <10 |
| 0.05% | SA | 8,700 | <10 | <10 | <10 | <10 |
| 0.10% | AN | <10 | <10 | <10 | <10 | <10 |
| 0.10% | CAN | <10 | <10 | <10 | <10 | <10 |
| 0.10% | EC | 10 | <10 | <10 | <10 | <10 |
| 0.10% | BC | <10 | <10 | <10 | <10 | <10 |
| 0.10% | PSA | <10 | <10 | <10 | <10 | <10 |
| 0.10% | SA | 60 | <10 | <10 | <10 | <10 |
| 0.20% | AN | <10 | <10 | <10 | <10 | <10 |
| 0.20% | CAN | <10 | <10 | <10 | <10 | <10 |
| 0.20% | EC | <10 | <10 | <10 | <10 | <10 |
| 0.20% | BC | <10 | <10 | <10 | <10 | <10 |
| 0.20% | PSA | <10 | <10 | <10 | <10 | <10 |
| 0.20% | SA | <10 | <10 | <10 | <10 | <10 |

Unpreserved Control

| Organism | 48 Hours | 7 Days | 14 Days |
|---|---|---|---|
| AN | 160,000 | 40,000 | 40,000 |
| CAN | 4,400,000 | 960,000 | 1,000,000 |
| EC | 100,000,000 | 1,000,000 | 1,000,000 |
| BC | 100,000,000 | 1,000,000 | 1,000,000 |
| PSA | 100,000,000 | 1,000,000 | 1,000,000 |
| SA | 27,000,000 | 9,1000 | 6,500 |

Inoculum Concentration

| Organism | 0 Hours | 21 Days |
|---|---|---|
| AN | 190,000 | 26,000 |
| CAN | 1,900,000 | 380,000 |
| EC | 4,600,000 | 700,000 |
| BC | 5,200,000 | 310,000 |
| PSA | 5,200,000 | 14,000,000 |
| SA | 8,400,000 | 960,000 |

TABLE XVII

Shampoo
2:98 DBDCB/Diazolidinyl Urea

| Test Level | Organism | 48 Hours | 7 Days | 14 Days | 21 Days | 28 Days |
|---|---|---|---|---|---|---|
| 0.025% | AN | 70,000 | <10 | <10 | <10 | <10 |
| 0.025% | CAN | <10 | <10 | <10 | <10 | <10 |
| 0.025% | EC | 460 | <10 | <10 | <10 | <10 |
| 0.025% | BC | <10 | <10 | <10 | <10 | <10 |
| 0.025% | PSA | <10 | <10 | <10 | <10 | <10 |
| 0.025% | SA | <10 | <10 | <10 | <10 | <10 |
| 0.05% | AN | 2,400 | <10 | <10 | <10 | <10 |
| 0.05% | CAN | <10 | <10 | <10 | <10 | <10 |
| 0.05% | EC | <10 | <10 | <10 | <10 | <10 |
| 0.05% | BC | <10 | <10 | <10 | <10 | <10 |
| 0.05% | PSA | <10 | <10 | <10 | <10 | <10 |
| 0.05% | SA | <10 | <10 | <10 | <10 | <10 |
| 0.10% | AN | <10 | <10 | <10 | <10 | <10 |
| 0.10% | CAN | <10 | <10 | <10 | <10 | <10 |
| 0.10% | EC | <10 | <10 | <10 | <10 | <10 |
| 0.10% | BC | <10 | <10 | <10 | <10 | <10 |
| 0.10% | PSA | <10 | <10 | <10 | <10 | <10 |
| 0.10% | SA | <10 | <10 | <10 | <10 | <10 |

Unpreserved Control

| Organism | 48 Hours | 7 Days | 14 Days |
|---|---|---|---|
| AN | 160,000 | 1800000 | 40,000 |
| CAN | 80 | 2300 | 3,000 |
| EC | 30,000 | 4100 | 40 |
| BC | 1,000,000 | 1,000,000 | 1,000,000 |
| PSA | 1,000,000 | 1,000,000 | 10,000 |
| SA | <10 | <10 | <10 |

Inoculum Concentration

| Organism | 0 Hours | 21 Days |
|---|---|---|
| AN | 110,000 | 70,000 |
| CAN | 460,000 | 5,700,000 |
| EC | 25,000,000 | 170,000 |
| BC | 74,000 | 3,800,000 |
| PSA | 3,900,000 | 2,300,000 |
| SA | 120,000 | 1,800,000 |

The results shown in Tables VII–XVII demonstrate that the compositions of the invention are completely effective against the tested organisms in comparison to the unpreserved controls.

As indicated above, it is only within the critical weight ratios and concentration ranges of (a) and (b) which are proscribed by this invention that the synergistic antimicrobial effect of the mixture can be increased at least 3 fold over that of the individual components when used alone at the same dosage level.

While the invention has been described with particular reference to certain embodiments thereof, it will be understood that changes and modifications may be made which are within the skill of the art. Accordingly, it is intended to be bound only by the following claims, in which:

What is claimed is:

1. A water soluble antimicrobial preservative composition consisting essentially of (a) from 0.5 to 20 wt. % of a terminally cyano-substituted dihalogenated alkane containing from 6 to 8 carbon atoms and (b) from 80 to 99.5 wt. % of a heterocyclic poly (hydroxylated lower alkylamide) having the formula:

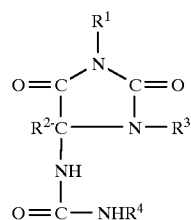

wherein each of $R^1$, $R^2$, $R^3$ and $R^4$ is independently lower alkyl, lower alkyl hydroxy or hydrogen with the proviso that at least two of $R^1$, $R^2$, $R^3$ and $R^4$ are lower alkyl hydroxy and the weight ratio of (a) to (b) is between 0.5:2 and 0.5:25, and wherein, lower alkyl in each instance, contains from 1 to 4 carbon atoms.

2. The composition of claim 1 wherein said alkane is a dihalo dicyano butane.

3. The composition of claim 2 wherein said dihalo dicyano butane has the formula

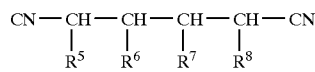

wherein two of $R^5$, $R^6$, $R^7$ and $R^8$ are halogen selected from the group consisting of chlorine, bromine and iodine and the remaining $R^5$, $R^6$, $R^7$ and $R^8$ are hydrogen.

4. The composition of claim 3 wherein said dihalo dicyano butane is 1,2-dibromo-1,4-dicyano butane.

5. The composition of claim 1 wherein said heterocyclic polyhydroxy lower alkyl amide is diazolidinyl urea having the formula:

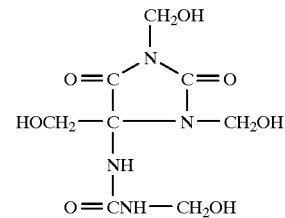

6. The composition of claim 1 wherein the composition is a free flowing powder.

7. The composition of claim 1 wherein the composition is a liquid dissolved in a solvent selected from the group consisting of a $C_1$ to $C_6$ alkanol, a $C_2$ to $C_4$ alkylene glycol, phenoxy ethanol and water.

8. The composition of claim 1 wherein the composition is an emulsion containing said mixture and an additive selected from the group consisting of an emulsifier, surfactant, and optionally a thickener.

9. A commercial formulation susceptible to microbial infection containing an effective antimicrobial amount of the composition of claim 1.

10. The formulation of claim 9 containing between about 0.01 and about 5 wt. % of the composition of any one of claims 1, 3, 4, or 5.

11. The formulation of claim 1 which is a cosmetic formulation.

12. The process of adding an effective antimicrobial amount of the composition of claim 1 to a substance infected with a fungus, algae, a gram-positive bacteria or a gram-negative bacteria.

13. The process of adding an effective antimicrobial amount of the composition of claim 1 to a substance susceptible to infection with fungi, algae, a gram-positive bacteria or a gram-negative bacteria.

14. The process of one of claims 12 or 13 containing between about 0.01 and about 5 wt. % of a mixture of from 0.5 to 12 wt. % dibromo dicyano butane and from 88 to 99.5 wt. % of diazolidinyl urea.

* * * * *